United States Patent [19]

Kelman

[11] 4,174,543

[45] Nov. 20, 1979

[54] INTRAOCULAR LENSES

[76] Inventor: Charles D. Kelman, 73 Bacon Rd., Old Westbury, N.Y. 11568

[21] Appl. No.: 911,452

[22] Filed: Jun. 1, 1978

[51] Int. Cl.² .......................... A61F 1/16; A61F 1/24
[52] U.S. Cl. ........................................................ 3/13
[58] Field of Search ........................................ 3/13, 1

[56] References Cited

U.S. PATENT DOCUMENTS

| 2,834,023 | 5/1958 | Lieb | 3/13 X |
| 4,087,866 | 5/1978 | Choyce et al. | 3/13 |

FOREIGN PATENT DOCUMENTS

| 959314 | 3/1957 | Fed. Rep. of Germany | 3/13 |
| 1034325 | 7/1958 | Fed. Rep. of Germany | 3/13 |

OTHER PUBLICATIONS

"Experience with Twelve Cases of Intra-Ocular Anterior Chamber Implants for Aphakia" by J. Boberg-Ans, British Journal of Ophthalmology, vol. 45, No. 1, Jan. 1961, pp. 37-43.

*Intraocular Lenses and Implants* by Peter Choyce, London, H. K. Lewis & Co., Ltd., 1964, pp. 13, 14 and 15.

"The Mark VI, Mark VII, and Mark VIII Choyce Anterior Chamber Implants", Proceedings of the Royal Society of Medicine, vol. 58, Sep. 1965, pp. 729-731.

*A Lens for all Seasons* by Jerald L. Tennant, Aug. 1976, pp. 4 & 35-67.

*Primary Examiner*—Ronald L. Frinks
*Attorney, Agent, or Firm*—Philip Rodman

[57] ABSTRACT

Intraocular lenses with four point position fixation in the eyeball have positioning elements that provide lens stability with respect to the pupil while being substantially deflectable in response to normal distortions of the eyeball to minimize eye irritation and other eyeball distortion related trauma.

16 Claims, 7 Drawing Figures

U.S. Patent   Nov. 20, 1979   4,174,543
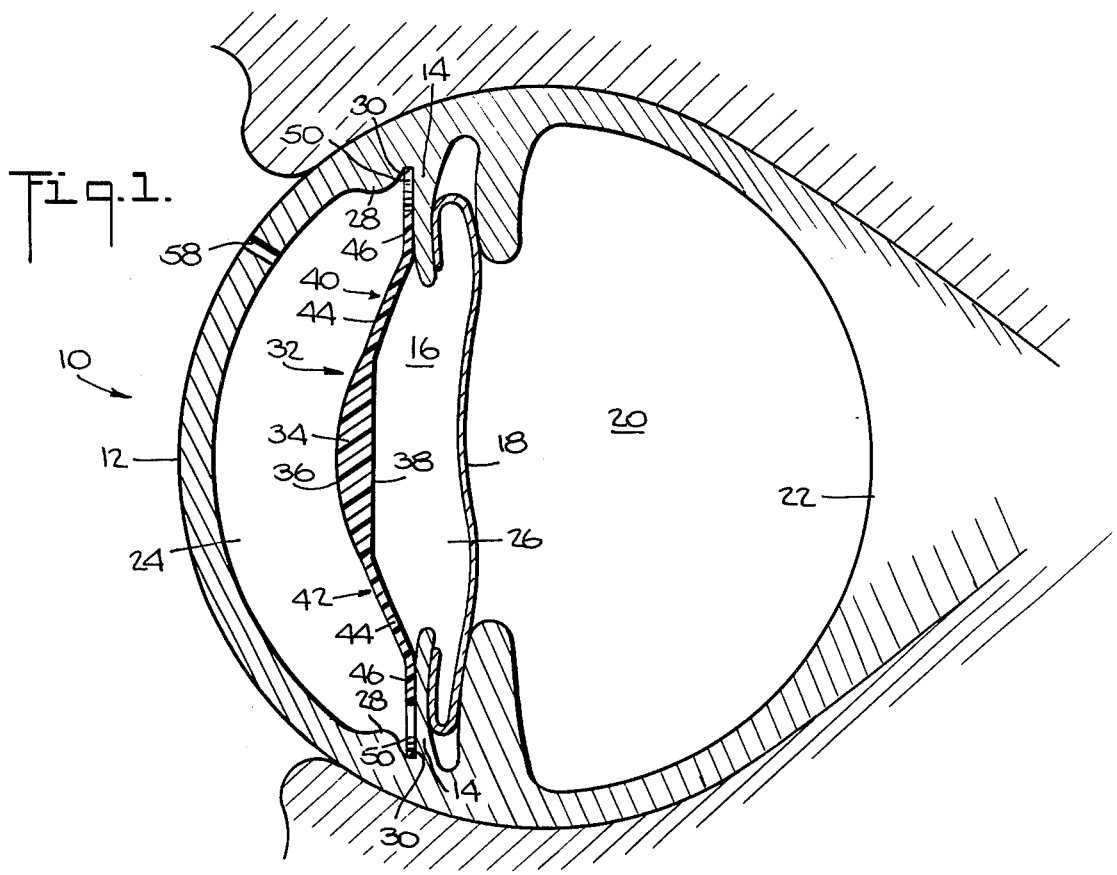
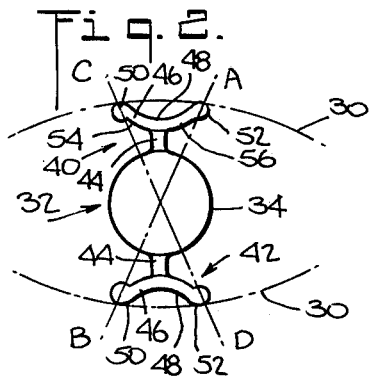 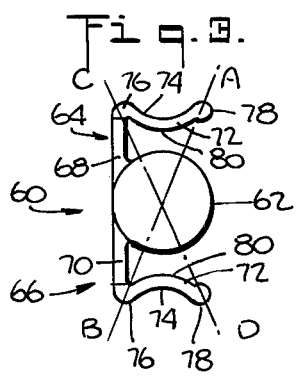 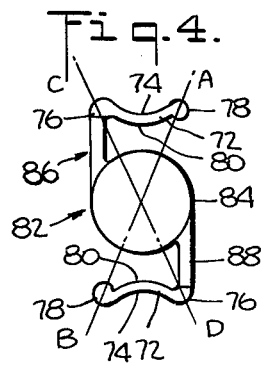
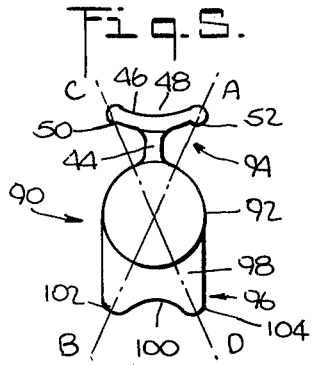 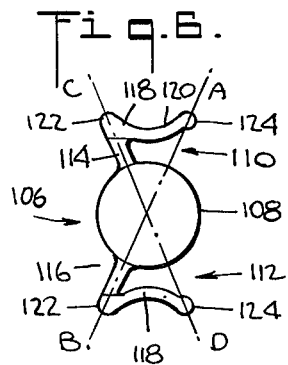 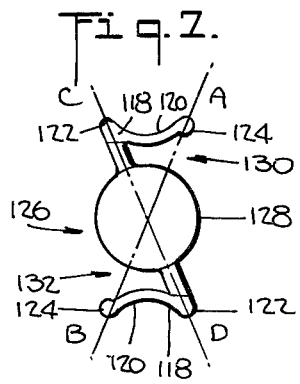

INTRAOCULAR LENSES

This invention relates to intraocular lenses for the human eye and more particularly to an intraocular lens that readily yields to normal distortions of the eye.

The replacement of a natural lens with an artificial intraocular lens implant in the human eye is a well known procedure within the medical profession. Techniques for accomplishing such replacement, as described and referred to in my copending application Ser. No. 791,693, filed Apr. 28, 1977 now U.S. Pat. No. 4,092,743, usually require a corneo-scleral incision through which the natural lens is removed and the artificial lens inserted. The inserted lens can be affixed in position in either the anterior or posterior chamber of the eye in accordance with techniques referred to in my copending patent application.

Intraocular lenses of known design and construction generally include a medial light focusing lens body provided with a support structure that is affixed to natural regions of the eye to align and stabilize the lens body with respect to the pupil. The support structure, depending upon its construction and location in the eye, can be affixed in position by sutures or by engagement with predetermined regions of the eye.

Once the intraocular lens is positioned in the eye it is desirable that the installation be of a permanent nature so that subsequent adjustments will not be necessary. Ideally any further need for vision correction, following an intraocular lens implant, should be accomplished with eyeglasses or any other known non-surgical procedures.

It is well known that activities such as walking, swimming, and jogging, rubbing or touching of the eyelids, and unexpected common physical jolts such as might be due to falls, or impacts upon various parts of the body, can cause the eyeball to distort. Distortion of an eyeball having an intraocular lens implant often produces intermittent stress on the lens support structure and the regions of the eye to which the support structure is affixed. These intermittent stresses can generally cause eye irritation, possible damage to the iris root or ciliary body, or other manifestation of trauma. While such eyeball distortion can be controlled to a certain extent by limiting one's physical activities, such distortion cannot be altogether eliminated.

Intraocular lenses such as shown in the publication entitled "Proceedings of the Royal Society of Medicine, Volume 58, September 1965" at page 731, have been known to allow a relatively stable affixation of an artificial lens in the eye. Such stability is attributable to a support structure having four lobes in paired arrangement, one pair engaging an upper portion of the eye and another pair engaging a lower portion of the eye to provide four point fixation within the anterior chamber of the eye. However since the full extent of the support structure is linked to the lens body it cannot deflect freely of the lens body, and there is a likelihood that stresses on the support structure due to eyeball distortion will irritate the regions of the eye that engage the support structure.

It is thus desirable to provide an intraocular lens having a support structure that readily yields to normal distortions of the eye to minimize any eye trauma attributable to distortion related stresses within the eye.

Among the several objects of the present invention may be noted the provision of an intraocular lens having position fixation means that are freely deflectable with respect to the lens body, an intraocular lens having position fixation means that include two pairs of contact lobes with at least one pair being capable of yielding independently of the other pair in response to normal distortions of the eye, and an intraocular lens that minimizes eye irritation resulting from distortion related stresses within the eye.

Other objects and features will be in part apparent and in part pointed out hereinafter.

The present invention resides in an intraocular lens capable of yielding to normal distortions to the eye to minimize eye irritation and other distortion related eye trauma.

In accordance with the invention, an intraocular insert comprises a medial light focusing lens body with two generally oppositely disposed position fixation elements that are formed integral with the lens body. At least one of the position fixation elements includes a stem portion extending from the periphery of the lens body and a limb portion joined to and extending from the stem portion. The limb portion includes a concave outer seating edge with a pair of contact lobes and an inner edge free from connection with the lens body. The other position fixation element also includes a concave outer seating edge with contact lobes formed at the end portions of the seating edge. The concavity of the seating edges ensure limited edge contact with the eye at the area of the contact lobes.

In several embodiments of the invention the stem and limb portions of the position fixation elements are symmetrically arranged. In other embodiments of the invention the stem and limb portions are of similar configuration but are arranged asymmetrically with respect to each other. In a further embodiment of the invention the second position fixation element has no separately definable stem and limb portions. In still other embodiments the stem portion joins with the limb portion at one end or intermediate the opposite ends of the limb portion.

In each of the foregoing embodiments at least one of the contact lobes on one of the seating edges deflects independently of the contact lobes on the other seating edge in directions toward and away from the lens body in response to normal distortions of the eye.

The invention accordingly comprises the constructions hereinafter described, the scope of the invention being indicated in the following claims.

In the accompanying drawing in which various possible embodiments of the invention are illustrated, FIG. 1 is a simplified schematic sectional view of an eyeball implanted with an intraocular insert incorporating one embodiment of the present invention; and, FIGS. 2–7 illustrate other embodiments of the invention.

Corresponding reference characters indicate corresponding parts throughout the several views of the drawing.

Referring to the drawing, reference number 10 generally indicates an eyeball as shown in simplified schematic cross-section in FIG. 1. Portions of the eyeball structure which are not believed essential to an understanding of the invention have been omitted for the sake of clarity.

The eyeball 10 includes a cornea 12, a diaphragm or iris 14 having a central opening or pupil 16, a membrane 18 confining a vitreous humor 20 and a retina 22. The natural lens, which normally occupies the area between the membrane 18 and the iris 14, has been omitted since the invention deals with artificial substitutes for a natural lens.

An aqueous zone, between the cornea 12 and the membrane 18, is subdivided by the iris 14 into an anterior chamber 24 and a posterior chamber 26. A scleral spur 28 in the anterior chamber 24 is spaced from the iris 14 thereby defining a groove 30.

An intraocular artificial insert for the eyeball 10 is generally indicated by reference number 32 in FIG. 1. The insert 32 can be formed of any suitable material which is compatible with the environment of the eyeball, such as a non-toxic plastic, for example, polymethylmethacrylate.

The insert 32 includes a medial light focusing lens body 34 having a convex or flat anterior surface 36 and a generally flat or convex posterior surface 38. A pair of oppositely disposed symmetrical position fixation elements 40 and 42 extend from opposite peripheral portions of the lens body 34.

The position fixation element 40 includes a stem portion 44 and a limb portion 46 joined at its mid-section to the stem portion 44. The limb portion 46 extends transversely of the stem portion 44 and has a concave outer seating edge 48 having opposite end portions that terminate with respective contact lobes 50 and 52. An inner edge portion of the limb 46, indicated by reference numbers 54 and 56, is free from connection with the lens body 34. The position fixation element 42, being symmetrical with the position fixation element 40, is designated with reference numbers that correspond to those of the described element 40.

The insert 32 can be located in the eyeball 10 using suitable known medical procedures that involve passing the insert structure into the anterior chamber 24 through a corneo-scleral incision 58 that is also used to remove the natural lens (not shown).

Preferably the insert 32 is fixed in position in the anterior chamber 24 by engagement of the contact lobes 50 and 52 of the position fixation element 40 with an upper portion of the groove 30, shown schematically in FIG. 2. The lower portion of the groove 30, also shown schematically in FIG. 2, receives the contact lobes 50 and 52 of the position fixation element 42. Under this arrangement a four point contact is provided between the insert 32 and the upper and lower portions of the groove 30.

The precise dimensions of the insert 32 may vary since they are based upon the dimensional characteristics of the eyeball 10 which are known to differ with different patients. Nevertheless to exemplify the magnitudes being dealt with, as disclosed in my copending application, the lens body 34 can be 0.4 millimeters thick with a diameter of 4 millimeters. The thickness of the position fixation elements 40 and 42 can be 0.2 millimeters, the width thereof about 1.2 millimeters, and the distance between corresponding contact lobes such as 50, 50 can be approximately 12 millimeters. The radius of curvature of the concave outer seating edge 48 can be approximately 180 millimeters.

It will be noted that the limb portions 46, 46 of the position fixation elements 40 and 42 are substantially coplanar and engage the iris 14. The posterior surface 38 of the lens body 34 lies in a plane that is parallel to the plane of the limb portions 46, 46 and is spaced therefrom by about 0.25 millimeters to 0.75 millimeters. This spacing is desirable to maintain the lens body 34 out of contact with the iris and to prevent the lens from interfering with expansion and contraction of the pupil 16. Therefore the stem portions 44, 44 are slightly inclined with respect to the posterior lens surface 38 and the limb portions 46, 46 as shown in FIG. 1.

While the overall end to end distance of the limb portion 46 can equal, exceed or be less than the diameter of the lens body 34 it should be borne in mind that the length of the limb portion 46 in excess of the lens body diameter may require a corneo-scleral incision 58 that is larger than the minimum incision necessary to accomodate insertion of the lens body 34.

Measurements of the eyeball that are usually made before surgery will determine the precise dimension of the insert 32 eventually selected for implantation.

When the insert 32 has been implanted in the eyeball 10, as shown in FIG. 1, the contact lobes 50 and 52 of the respective position fixation elements 40 and 42 seat against the upper and lower groove portions 30 as shown in FIG. 2 to provide four point contact. The concave outer seating edge 48 between the lobes 50 and 52 does not engage the upper and lower groove portions 30.

Under this arrangement there is sufficient flexibility of the position fixation elements 40 and 42 to permit deflection of the respective contact lobes 50 and 52 along the diagonal lines AB and CD as shown in FIG. 2. The insert 32 will thus yield to normal distortions of the eyeball due to slight rubbing, and other previously described activities that tend to cause such distortion.

When using an insert 32 having an overall length of 12.5 millimeters along the diagonals AB or CD, for example, the diametrically opposed contact lobes are capable of deflecting a distance of 2-3 millimeters along the lines AB and/or CD. As a result of such deflection capability the possibility of irritation of the iris 14 or the tissue in the upper and lower groove portions 30 is minimized because the contact lobes 50 and 52 on the position fixation element 40 can deflect independently of the contact lobes 50 and 52 on the position fixation element 42. Moreover, the deflections of the position fixation elements 40 and 42 will not upset the alignment between the lens body 34 and the pupil 16.

Although not shown, one or both of the limb portions 46, 46 can be secured to the iris 14 using suturing procedures referred to in my copending application or any other suitable known affixation technique.

In another embodiment of my invention, an intraocular insert is generally indicated by the reference number 60 in FIG. 3. The insert member 60 includes a medial light focusing lens body 62 and a pair of oppositely disposed symmetrical position fixation elements 64 and 66. The position fixation elements 64 and 66 include respective stem portions 68 and 70 that are cotangent to the periphery of the lens body 62.

The stem portions 68 and 70 each include an identical limb portion 72, 72 joined thereto in cantilever arrangement. A concave outer seating edge 74 of one of the limbs 72 terminates with respective contact lobes 76 and 78. Under this arrangement an inner edge portion 80 of the limb 72 is free from connection with the periphery of the lens body 62.

The dimensions associated with the intraocular insert 32 are similarly applicable to the intraocular insert 60. However, the provision of an end to end length of the limb portion 72 in excess of the diameter of the lens body 62 would not necessitate an enlargement of the corneo-scleral incision beyond the minimum required for insertion of the lens body 62 since the position fixation elements 64 and 66 can be snaked into the incision in a manner described in my copending patent application.

When the insert member 60 is implanted in the eyeball the limb portion 72 of the position fixation element 64 will engage an upper portion of the groove 30 and the limb portion 72 of the position fixation element 66 engages a lower portion of the groove 30. The contact lobe 78 is thus free to deflect toward and away from the periphery of the lens body 62 in response to normal distortions of the eyeball as previously described. The contact lobe 76, which joins with the stem portion 68, can also deflect in response to distortions of the eye but has less freedom than the contact lobe 78 because it is linked directly to the lens body 62. It will be apparent that the deflection capability of the position fixation elements 64 and 66 along the diagonal AB is substantially equivalent to the deflection capability along the diagonal CD.

In a further embodiment of my invention, an intraocular insert is generally indicated by the reference number 82 in FIG. 4. The insert member 82 includes a medial light focusing lens body 84 and a pair of oppositely disposed similarly constructed but asymmetrically arranged position fixation elements 86 and 88 joined to opposite portions of the lens periphery. The position fixation element 86 is identical to the position fixation element 64 of the FIG. 3 embodiment, whereas the position fixation element 88 is in a reverse position with respect to the position fixation element 66 of the FIG. 3 embodiment.

The intraocular location of the position fixation elements 86 and 88 is carried out in a manner similar to that previously described for the FIG. 3 embodiment. It will be apparent from the arrangement of the position fixation elements 86 and 88 that deflection along the diagonal AB will occur more readily than along the diagonal CD. Nevertheless, the ability of the insert member 82 to deflect along both diagonals AB and CD in response to normal distortions of the eye is present.

In still another embodiment of my invention, an intraocular insert is generally indicated by the reference number 90 in FIG. 5. The insert member 90 includes a medial light focusing lens body 92 and a pair of oppositely disposed dissimilar position fixation elements 94 and 96 joined to opposite portions of the lens periphery. The position fixation element 94 is identical to the position fixation element 40 of FIG. 2. The position fixation element 96 comprises a web 98 having a concave outer seating edge 100 that terminates with contact lobes 102 and 104.

As indicated, with regard to the FIG. 2 embodiment, the end to end distance of the limb portion 46 of the position fixation element 94, and the end to end distance of the outer seating edge 100 of the position fixation element 96 can exceed the diameter of the lens body 92. However, when said dimensions exceed the diameter of the lens body 92 a corneo-scleral incision larger than the minimum incision necessary to accommodate insertion of the lens body 92 will be required.

The intraocular location of the position fixation elements 94 and 96 in the eyeball is carried out in a manner similar to that previously described. Since the contact lobes 50 and 52 are free to deflect with respect to the lens periphery whereas equivalent freedom is not present in the position fixation element 96 it will be apparent that deflection of the insert 90 along the diagonals AB and CD occurs predominantly at the limb portion 46 of the position fixation element 94.

If desired a perforation or plurality of perforations, can be provided in the position fixation element 96 to facilitate suturing and/or handling of the insert 90 during implantation.

In another embodiment of my invention an intraocular insert is generally indicated by the reference number 106 in FIG. 6. The insert member 106 includes a medial light focusing lens body 108 and a pair of oppositely disposed symmetrical position fixation elements 110 and 112 joined to the lens periphery. The position fixation elements 110 and 112 include stem portions 114 and 116 that will intersect with each other if projected toward the center of the lens body 108.

The stem portions 114 and 116 each include an identical limb portion 118 joined thereto in cantilever arrangement. A concave outer seating edge 120 of one of the limbs 118 terminates with respective contact lobes 122 and 124. The intraocular location of the position fixation elements 110 and 112 is carried out in a manner similar to that described for the FIG. 3 embodiment. It will be apparent from the symmetrical arrangement of the position fixation elements 110 and 112 that the deflection capability of the contact lobes 122 and 124 along the diagonal AB is substantially equivalent to the deflection capability along the diagonal CD.

In a further embodiment of my invention an intraocular insert is generally indicated by the reference number 126 in FIG. 7. The insert member 126 includes a medial light focusing lens body 128 and a pair of oppositely disposed, similarly constructed, but asymmetrically arranged position fixation elements 130 and 132 joined to opposite portions of the lens periphery. The position fixation element 130 is identical to the position fixation element 110 of the FIG. 6 embodiment, whereas the position fixation element 132 is in a reverse position with respect to the position fixation element 112 of the FIG. 6 embodiment.

The intraocular location of the position fixation elements 130 and 132 is carried out in a manner similar to that described for the FIG. 3 embodiment. It will be apparent from the arrangement of the position fixation elements, 130 and 132 that deflection along the diagonal AB will occur more readily than along the diagonal CD, but deflection capability is present along both diagonals in response to normal distortions of the eyeball.

Some advantages of the present invention evident from the foregoing description include an intraocular lens, with four point position fixation in the eyeball, that provides lens stability with respect to the pupil and relatively substantial deflectability of the position fixation elements to help minimize eye irritation and other eyeball distortion related trauma attributable to an intraocular lens implant.

In accordance with selected embodiments of my invention the deflectability of the position fixation elements can be more pronounced along one of two diagonals that pass through a central portion of the lens body and connect oppositely disposed contact lobes, or such deflectability can be equivalent along both diagonals. In addition the position fixation elements on one insert can be of different construction so that one element has a greater deflectability along the diagonals than the other element has. Thus the amount of deflection of the intraocular insert can be controlled along predetermined directions depending upon the embodiment of the invention that is selected for use. A further advantage is that several embodiments of the invention can be passed through a corneo-scleral incision that is the minimum size necessary to accommodate the lens body.

In view of the above it will be seen that the several objects of the invention are achieved and other advantageous results attained.

As various changes could be made in the above constructions without departing from the scope of the invention, it is intended that all matter contained in the above description or shown in the accompanying drawing shall be interpreted as illustrative and not in a limiting sense.

What is claimed is:

1. An intraocular insert suitable for use as an artificial lens implant in the anterior chamber of a human eye, said anterior chamber having a groove between the scleral spur and the iris of the eye circumferentially and at upper and lower portions of the eye when viewed in cross section, said insert having a medial light focusing lens body having a periphery and generally oppositely disposed first and second position fixation means engageable with said respective upper and lower groove portions to fix the position of the lens body with respect to the pupil of the eye, said upper and lower groove portions having respective interior peripheral surfaces, said first and second position fixation means being integrally joined to predetermined first and second peripheral portions respectively of said lens body and respectively extending generally radially outwardly of said lens body, said first and second position fixation means respectively having first and second outer seating edges, each said outer seating edge respectively having a pair of spaced contact portions for paired contact with a respective one of said interior peripheral surfaces of said groove and a concave portion between said pair of contact portions that is normally free from contact with said respective ones of said interior peripheral surfaces of said groove, at least one of the position fixation means having a first stem portion integrally joined to and extending from one of said peripheral portions of said lens body, and a first limb portion joined to and extending from said first stem portion and including at least one free end having one of said contact portions, said first limb portion having a first radially outermost peripheral edge that defines one of said outer seating edges and a first inner edge free from connection with said lens body from said first stem to said one of said contact portions, at least one of said first stem portion and said first limb portion being of a first predetermined width and thickness to permit movement of said one of said contact portions toward and away from said lens body in response to normal distortions of the eye.

2. An intraocular insert as claimed in claim 1 wherein the first and second peripheral portions of said lens body are opposite each other on said lens periphery.

3. An intraocular insert as claimed in claim 1 wherein said other position fixation means has a second stem portion integrally joined to and extending from said other peripheral portion of said lens body, and a second limb portion joined to and extending from said second stem portion and including at least one free end having a second of said contact portions, said second limb portion having a second radially outermost peripheral edge that defines the other said outer seating edge and a second inner edge free from connection with said lens body from said second stem to said second contact portion, at least one of said second stem portion and said second limb portion being of a second predetermined width and thickness to permit movement of said second contact portion toward and away from said lens body in response to normal distortions of the eye.

4. An intraocular insert as claimed in claim 3 wherein said first and second stem portions are substantially parallel.

5. An intraocular insert as claimed in claim 3 wherein said first and second stem portions are substantially skew.

6. An intraocular insert as claimed in claim 3 wherein said first and second position fixation means are substantially symmetrical.

7. An intraocular insert as claimed in claim 3 wherein said first and second position fixation means are of similar construction but asymmetrically arranged on said lens body.

8. An intraocular insert as claimed in claim 3 wherein said first and second position fixation means are of dissimilar construction.

9. An intraocular insert as claimed in claim 1 wherein said first stem portion is joined to one end of said first limb portion in cantilever arrangement.

10. An intraocular insert as claimed in claim 1 wherein said first limb has a mid portion and said first stem portion is joined to the mid portion of said first limb portion whereby said first limb portion has opposite free ends.

11. An intraocular insert as claimed in claim 1 wherein the first and second position fixation means are arranged on said lens body to permit enclosure of said insert in a rectangle having a short side which is equal in dimension to the maximum crosswise dimension of said lens body and a long side which is equal in dimension to the distance between corresponding contact portions on said first and second outer seating edges.

12. An intraocular insert as claimed in claim 11 wherein said lens body has a generally circular periphery and the short side of said rectangle is equal in dimension to the diameter of said lens body.

13. An intraocular insert as claimed in claim 1 wherein said second position fixation means comprises a web portion extending from the second peripheral portion of said lens body, said web portion having opposite side edges defining opposite ends of said second outer seating edge.

14. An intraocular insert as claimed in claim 3 wherein said first stem portion is joined to one end of said first limb portion in cantilever arrangement.

15. An intraocular insert as claimed in claim 14 wherein said second stem portion is joined to one end of said second limb portion in cantilever arrangement.

16. An intraocular insert as claimed in claim 15 wherein said free ends of said first and second limb portions are located on the same side of said lens body.

* * * * *